US010217251B2

United States Patent
Krauss et al.

(10) Patent No.: US 10,217,251 B2
(45) Date of Patent: Feb. 26, 2019

(54) METHOD FOR IMAGE RECONSTRUCTION

(71) Applicant: Siemens Healthcare GmbH, Erlangen (DE)

(72) Inventors: Bernhard Krauss, Burgthann (DE); Rainer Raupach, Heroldsbach (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 63 days.

(21) Appl. No.: 15/464,694

(22) Filed: Mar. 21, 2017

(65) Prior Publication Data
US 2017/0278279 A1    Sep. 28, 2017

(30) Foreign Application Priority Data

Mar. 22, 2016 (DE) .......................... 10 2016 204 709

(51) Int. Cl.
*A61B 6/00* (2006.01)
*A61B 6/03* (2006.01)
(Continued)

(52) U.S. Cl.
CPC ............ *G06T 11/006* (2013.01); *A61B 6/032* (2013.01); *A61B 6/4241* (2013.01); *A61B 6/461* (2013.01);
(Continued)

(58) Field of Classification Search
CPC ..... G06T 11/006; G06T 7/0012; A61B 6/032; A61B 6/461; A61B 6/5205
See application file for complete search history.

(56) References Cited

U.S. PATENT DOCUMENTS 7,050,533 B2 * 5/2006 Heismann .............. A61B 6/032
378/18
7,856,134 B2 * 12/2010 Ruhrnschopf ......... A61B 6/032
382/128
(Continued)

FOREIGN PATENT DOCUMENTS

DE    102005028216 A1    12/2006
DE    102011083727 A1    4/2013

OTHER PUBLICATIONS

Alvarez, Robert E. et al.: Energy-selective Reconstructions in X-ray Computerized Tomography, Phys. Med. Biol., 1976, vol. 21, No. 5, pp. 733-744.
(Continued)

*Primary Examiner* — Kim Y Vu
*Assistant Examiner* — Molly Delaney
(74) *Attorney, Agent, or Firm* — Harness, Dickey & Pierce, P.L.C.

(57) ABSTRACT

A method for image reconstruction is disclosed, based upon a first plurality of spectral raw data sets. The method includes forming a second plurality of virtual raw data sets; reconstructing an auxiliary image data set on the basis of a virtual raw data set. A first material is selected from a material group which comprises a plurality of materials. Material-specific maps are generated for a number of second materials of the material group. A determination of material line integrals take place, for the second materials with forward projection of the respective material-specific map. Subsequently, synthetic projection data sets are determined for each material. Finally, a reconstruction of at least one image data set takes place on the basis of the synthetic projection data sets for a number of materials of the material group. An image reconstruction device and a computed tomography system are also disclosed.

25 Claims, 3 Drawing Sheets

(51) Int. Cl.
*G06T 7/00* (2017.01)
*G06T 11/00* (2006.01)

(52) U.S. Cl.
CPC ............ *A61B 6/482* (2013.01); *A61B 6/5205* (2013.01); *G06T 7/0012* (2013.01); *G06T 2207/10081* (2013.01)

(56) References Cited

U.S. PATENT DOCUMENTS

| | | | |
|---|---|---|---|
| 7,940,884 B2* | 5/2011 | Bruder | G06T 11/006 378/4 |
| 9,589,336 B2* | 3/2017 | Flohr | A61B 6/032 |
| 9,872,662 B2* | 1/2018 | Raupach | A61B 6/032 |
| 2006/0203956 A1 | 9/2006 | Raupach | |
| 2006/0285630 A1 | 12/2006 | Bernhardt et al. | |
| 2009/0086883 A1* | 4/2009 | Harer | A61B 6/032 378/4 |
| 2013/0083989 A1 | 4/2013 | Flohr et al. | |

OTHER PUBLICATIONS

R. Raupach et al., "An Image-based Beam Hardening Correction Technique for CT Images", RSNA 2001, Chicago; 2001.
German Office Action 10 2016 204 709.4 dated Nov. 14, 2016.

\* cited by examiner

METHOD FOR IMAGE RECONSTRUCTION

PRIORITY STATEMENT

The present application hereby claims priority under 35 U.S.C. § 119 to German patent application number DE 102016204709.4 filed Mar. 22, 2016, the entire contents of which are hereby incorporated herein by reference.

FIELD

At least one embodiment of the invention generally relates to a method for image reconstruction, an image reconstruction device and/or a computed tomography system.

BACKGROUND

During the projection of X-rays through an examination object, dependent upon the spectrum used and the materials to be penetrated, different absorption and scattering behavior occurs, wherein the low energy components in the spectrum are absorbed faster than the high energy components (radiation hardening). The X-ray radiation detected behind the examination object therefore contains information concerning the material properties of the examination object. In computed tomography systems (CT systems) with simultaneous detection of a plurality of spectra of the X-ray radiation, following the acquisition of projection data, image data sets can be reconstructed which contain information regarding the materials contained in the examination object. "Different X-ray energies" is to be understood as the detection of X-ray radiation with different X-ray energy spectra. This can be achieved, firstly, in that the X-ray source is operated with different voltages. Therefore, normally an X-ray energy is also simply denoted with the X-ray voltage (in kV) that has been set. Secondly, individual regions of the projected X-ray spectrum can be detected selectively in portions of a detector intended therefor. An energy predetermined for the representation or evaluation must not necessarily correspond to the actually detected energy of the projected X-ray spectrum, but can also be determined freely by way of an interpolation within a particular range. Herein the image data sets should be reconstructed as free as possible from artifacts caused by the radiation hardening.

From the document DE 10 2005 008 767 A1, there is known a raw data-based correction method wherein from a number of different detected spectral regions of the X-ray radiation, an image can be reconstructed in which radiation hardening artifacts are substantially suppressed. For this purpose, for each material component a transmission thickness is determined as the measured value, wherein the different components have different energy-dependencies of the absorption coefficients. The transmission thicknesses are consequently summed weighted to a pseudomonochromatic measured value. From these pseudomonochromatic measured values, an image is then reconstructed in which the radiation hardening artifacts are substantially suppressed. For simplification of the image reconstruction, therefore, the spectrally different measured values for the material components are grouped together to a pseudomonochromatic measured value.

Another image data-based approach known from practice is the separate radiation hardening correction for each measured region of the X-ray spectrum. For this purpose, initially a first reconstruction is undertaken and a base material is selected. In the first reconstruction, with the aid of a segmentation, those voxels which have admixtures of other base materials are identified. Although this succeeds in reducing the radiation hardening artifacts, the accuracy of the quantitative representation of the material properties (attenuation contributions or proportions) is restricted so that the images with reduced radiation hardening do not necessarily correspond to a consistent monochromatic image. This limitation applies particularly to the separation of more than two materials. Furthermore, variations of the spectrum over the field of view, for example, through shaping filters cannot be taken into account in practice.

SUMMARY

Embodiments of the present invention provides a method for image reconstruction, an image reconstruction device and a computed tomography system with which improved imaging is possible.

At least one embodiment is directed to an image reconstruction method; at least one embodiment is directed to an image reconstruction device and at least one embodiment is directed to a computed tomography system.

At least one embodiment is directed to a method for image reconstruction based upon a first plurality of spectral raw data sets which are each associated with different X-ray spectra, comprising:

Firstly, in a step a) the spectral raw data sets are combined to form a second plurality of virtual raw data sets. On the basis of a virtual raw data set, in a step b), an auxiliary image data set is reconstructed in each case. Subsequently, in a step c), a first material is selected from a material group which comprises a plurality of materials. For a number of second materials of the material group, in a step d), material-specific maps are generated from the auxiliary image data sets of the second materials. Using forward projection of the respective material-specific map, in a step e), material line integrals are determined for the second materials. In a step f), on this basis and on the basis of the virtual raw data sets, synthetic projection data sets are determined for each material. Finally, in a step g), at least one image data set is reconstructed on the basis of the synthetic projection data sets for a number of materials of the material group.

An image reconstruction device according to an embodiment of the invention comprises a data input interface, a data output interface and is configured so that for a first plurality of spectral raw data sets received via the data input interface, a method according to the invention for image reconstruction is carried out. For this, it preferably also comprises a combination module and an optimization module. Preferably, the image reconstruction device also comprises an input interface. The input interface receives input values as parameters for the method according to the invention. With this, for example, the material to be selected, the manner and means of the combination of spectral raw data sets to form virtual raw data sets, the number of iteration steps or the like can be stipulated.

The computed tomography system according to an embodiment of the invention includes at least one source detector arrangement which comprises an X-ray radiation source and a detector and is configured so that the detector receives radiation emitted from the X-ray radiation source in different original spectral channels as spectral raw data sets. The computed tomography system also has an image reconstruction device according to the invention. Preferably, the spectral raw data sets are transferred by a raw data output interface of the source detector arrangement to the image reconstruction device, the data input interface of which is connected to the raw data output interface to receive the spectral raw data sets.

A realization largely through software has the advantage that conventionally used image reconstruction devices can also be upgraded easily with a software update in order to operate in the manner according to an embodiment of the invention. At least one embodiment of the invention is therefore directed to a computer program product with a computer program which can be loaded directly into a memory storage facility of an image reconstruction device of a computed tomography system, having program portions in order to carry out all the steps of the method according to at least one embodiment of the invention when the program is executed in the image reconstruction device. Such a computer program product can comprise, apart from the computer program additional components, if relevant, such as, for example, documentation and/or additional components including hardware components, for example, hardware keys (dongles, etc.) in order to use the software.

For transport to the image reconstruction device and/or for storage at or in the image reconstruction device, a computer-readable medium, for example, a memory stick, a hard disk or another transportable or firmly installed data carrier can be used on which the program steps of the computer program which are readable and executable by a computer unit of the image reconstruction device are stored. For this purpose, the computer unit can have one or more cooperating microprocessors or the like.

BRIEF DESCRIPTION OF THE DRAWINGS

The invention will now be described again in greater detail using example embodiments by reference to the accompanying drawings. In the various drawings, the same components are provided with identical reference signs. The drawings are in principle not to scale.

In the drawings.

DETAILED DESCRIPTION OF THE EXAMPLE EMBODIMENTS

Figure 1:
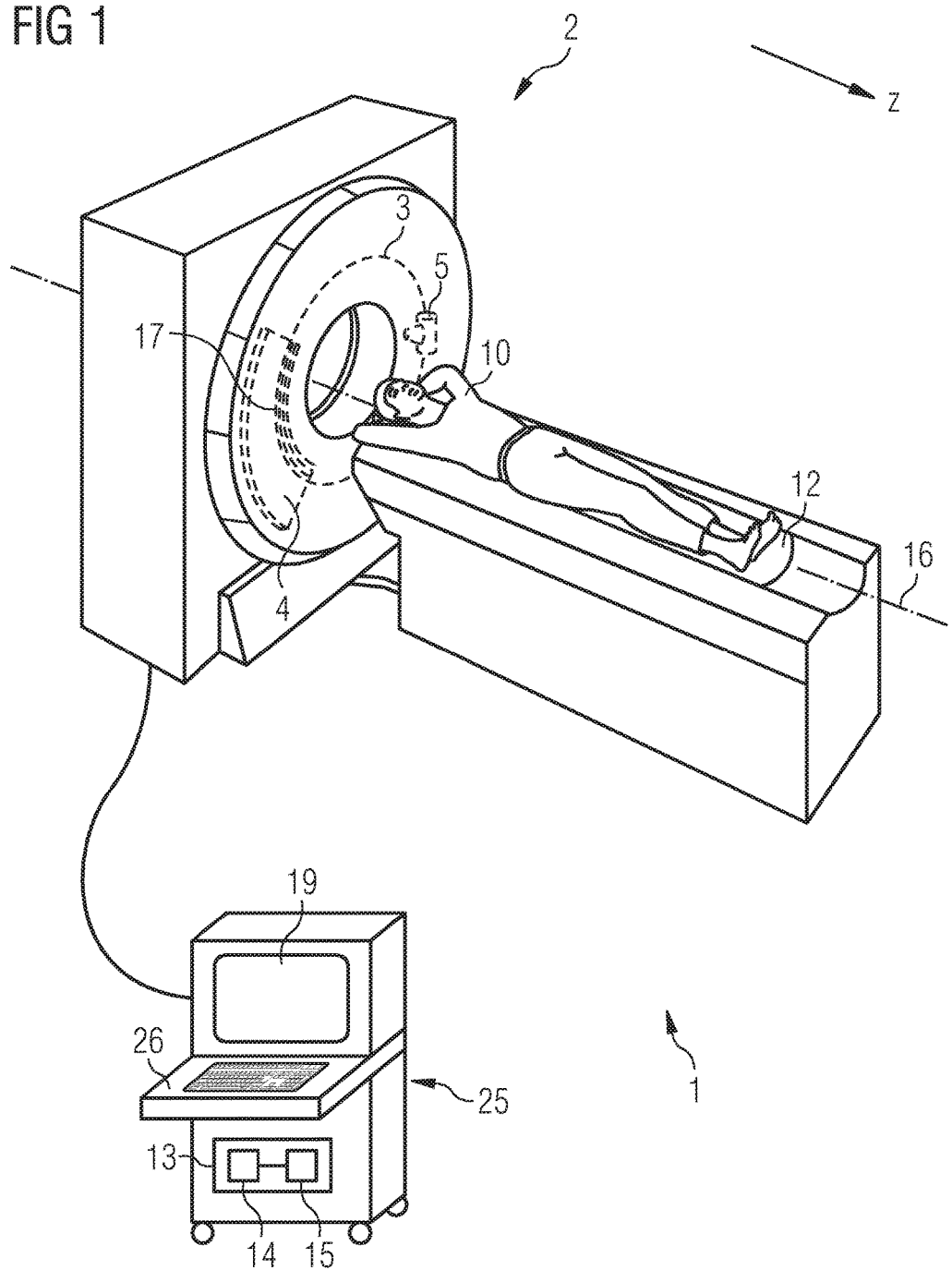
FIG. 1 is a schematic representation of an example embodiment of a computed tomography system according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment is directed to a method for image reconstruction based upon a first plurality of spectral raw data sets which are each associated with different X-ray spectra, comprising:

Firstly, in a step a) the spectral raw data sets are combined to form a second plurality of virtual raw data sets. On the basis of a virtual raw data set, in a step b), an auxiliary image data set is reconstructed in each case. Subsequently, in a step c), a first material is selected from a material group which comprises a plurality of materials. For a number of second materials of the material group, in a step d), material-specific maps are generated from the auxiliary image data sets of the second materials. Using forward projection of the respective material-specific map, in a step e), material line integrals are determined for the second materials. In a step f), on this basis and on the basis of the virtual raw data sets, synthetic projection data sets are determined for each material. Finally, in a step g), at least one image data set is reconstructed on the basis of the synthetic projection data sets for a number of materials of the material group.

The spectral raw data sets herein represent projection data of an examination object which—preferably via a CT device—has been acquired from a plurality of different projection angles. The spectral raw data sets are herein acquired dependent upon the detected X-ray spectrum, i.e. associated with the energy spectrum or the wavelength region of the projected X-ray radiation, in each case in an "original" or real (in contrast to the later defined virtual) "spectral channel". This can take place by way of various multi-energy CT approaches, for example, dual-source, split-filter or kV-switching and the like. Preferably, for this purpose, the CT device has a quantum-counting detector which detects the X-ray radiation dependent upon its energy thresholds in separate bins which therefore form the original spectral channels.

The plurality N of spectral raw data sets is therefore defined by way of the number of different original spectral channels. They are initially combined to form a second, preferably identical or smaller, plurality M of "virtual" raw data sets. This can take place, for example, by way of a linear combination of the spectral raw data sets, that is, by a weighted addition with definable weighting coefficients. The virtual raw data sets are thus put together with a new virtual spectrum and therefore are also preferably assigned to a "virtual" spectral channel with which a material is also preferably associated. This step serves to bring the data for the subsequent steps into as favorable a form as possible, as will be described in detail below.

From the virtual raw data sets, with the aid of a common reconstruction method such as filtered back projection, auxiliary image data sets are calculated. The auxiliary image data sets are substantially three-dimensional images of the examination object as would be generated on regular reconstruction of a raw data set obtained in an acquisition under an X-ray spectrum that has previously been modified as described above.

The number M of auxiliary image data sets—that is the number M of virtual raw data sets—corresponds to the number M of materials of the material group. The material group contains the materials which are subsequently taken into account in the reconstruction according to the invention. A material can be a chemical element, for example calcium, or a substance, for example water. In general, it thus represents relatively complex structural compositions in the examination object, for example bone, soft tissues, etc. However, a contrast medium, for example gadolinium, can be added as an additional material for the data acquisition in order to emphasize particular structures such as vessels, etc.

From the material group, a first material is selected for which subsequently no material-specific map is generated. The other materials are the two materials of the material group for which material-specific maps are generated. The material-specific maps herein represent material density distributions which are determined taking account of local attenuation contributions of the material-dependent attenuation coefficients from the auxiliary image data sets voxel-wise, i.e. volume image point by volume image point. By way of the spectrally-dependent spatially-resolved attenuation of the X-ray radiation, therefore, the respective material concentrations in the examination object can be localized. In order to determine the material-specific maps more accurately, the auxiliary image data set can be processed with the aid of a further-reaching image analysis, as described in detail below.

The forward projection of the material-specific maps is preferably modeled with the same geometry as the virtual raw data sets. Thus, virtual projections of the individual material maps are generated which correspond to the scanning arrangement during the original acquisition. In contrast to the method known from practice, in the context of the invention, the projection geometry is taken into account. This virtual forward projection delivers line integrals, the so-called material line integrals as the result for each of the second materials. These each represent the integrated material component on the projection route.

With the aid of the material line integrals, an imaging function for determining the optimized synthetic projection data sets is generated. In this imaging function, the virtual raw data sets thus represent the arguments of the function. The imaging function therefore acts as a reconstruction matrix with the use of which optimized synthetic projection data sets are created from the virtual raw data sets.

This is based on the following consideration. In a predetermined spectrum, a measured value can be determined as a first function in the form of a (linear) combination of the material line integrals for the respective materials. The material line integrals are thus components of the first function. Due to its strict monotonicity, the first function can be inverted, for example, in its first component (the first component is herein assigned to the first material). This means that the material line integral of the first material can be represented as an inverse function from the first function and the remaining material line integrals. Herein, the first function is however the measured value itself. The inverse function (the material line integral of the first material) is thus dependent on the measured value and the remaining material line integrals.

The imaging functions each generate a synthetic projection data set, that is, synthetic measured values. For these also, therefore, the above construction rules apply. The first component is herein expressed in the form of the above described inverse function, that is, dependent upon the virtual raw data sets as measured values and dependent upon the other material line integrals. The remaining components arise from the remaining material line integrals. The absorption coefficients assigned to each material serve as the coefficients of the individual components.

From the synthetic projection data prepared in this way, finally by way of a common reconstruction method such as filtered back projection, at least one image data set is reconstructed, but preferably one image data set for each material.

In an embodiment of the invention, the data is thus not reduced at the start to a pseudomonoenergetic data set, rather the number M of virtual raw data sets or of synthetic projection data sets remains the same and each set of virtual raw data is individually monochromatized optimally by way of its own imaging function.

An image reconstruction device according to an embodiment of the invention comprises a data input interface, a data output interface and is configured so that for a first plurality of spectral raw data sets received via the data input interface, a method according to the invention for image reconstruction is carried out. For this, it preferably also comprises a combination module and an optimization module. Preferably, the image reconstruction device also comprises an input interface. The input interface receives input values as parameters for the method according to the invention. With this, for example, the material to be selected, the manner and means of the combination of spectral raw data sets to form virtual raw data sets, the number of iteration steps or the like can be stipulated.

The computed tomography system according to an embodiment of the invention includes at least one source detector arrangement which comprises an X-ray radiation source and a detector and is configured so that the detector receives radiation emitted from the X-ray radiation source in different original spectral channels as spectral raw data sets. The computed tomography system also has an image reconstruction device according to the invention. Preferably, the spectral raw data sets are transferred by a raw data output interface of the source detector arrangement to the image reconstruction device, the data input interface of which is connected to the raw data output interface to receive the spectral raw data sets.

The essential components, in particular the combination module and the optimization module, of the image reconstruction device according to embodiments of the invention can be configured mainly in the form of software components. Fundamentally however, these components can also, in part, be realized especially, if particularly rapid calculations are involved, in the form of software-supported hardware, for example, FPGAs or the like. Similarly, the required interfaces can be configured, for example, where only an acceptance of data from other software components is concerned, as software interfaces. However, they can also be configured as interfaces constructed from hardware, which are controlled by suitable software.

In particular, the image reconstruction device according to an embodiment of the invention can be part of a user terminal or a control device of a computed tomography system.

A realization largely through software has the advantage that conventionally used image reconstruction devices can also be upgraded easily with a software update in order to operate in the manner according to an embodiment of the invention. At least one embodiment of the invention is therefore directed to a computer program product with a computer program which can be loaded directly into a memory storage facility of an image reconstruction device of a computed tomography system, having program portions in order to carry out all the steps of the method according to at least one embodiment of the invention when the program is executed in the image reconstruction device. Such a computer program product can comprise, apart from the computer program additional components, if relevant, such as, for example, documentation and/or additional components including hardware components, for example, hardware keys (dongles, etc.) in order to use the software.

For transport to the image reconstruction device and/or for storage at or in the image reconstruction device, a computer-readable medium, for example, a memory stick, a hard disk or another transportable or firmly installed data carrier can be used on which the program steps of the computer program which are readable and executable by a computer unit of the image reconstruction device are stored. For this purpose, the computer unit can have one or more cooperating microprocessors or the like.

Further particularly advantageous embodiments and developments of the invention are disclosed by the dependent claims and the following description, wherein the independent claims of one claim category can also be developed similarly to the dependent claims of another claim category and, in particular, also individual features of different example embodiments or variants can be combined to form new example embodiments or variants.

In one advantageous example embodiment of the method according to the invention, the spectral raw data sets are combined to form the virtual raw data sets such that the virtual raw data sets have defined mean energies. The fact that the virtual raw data sets have defined mean energies means that they comprise virtual measured values with the defined mean energy, as described below. In general, raw data sets contain a set of projection data composed also pixel-wise from a plurality of measured values. The real measured values of the spectral raw data sets detected dependent upon their energy are combined pixel-wise during the combination of the spectral raw data sets so that the resultant virtual measured values have a defined mean energy. The defined mean energies can herein be specified by a user or stipulated dependent upon specific properties of the materials, such as absorption coefficients, etc.

In a further advantageous example embodiment of the method according to the invention, the spectral raw data sets are combined to form the virtual raw data sets such that the virtual raw data sets have defined effective energies. The combination takes place as already defined above, but with effective energies in place of mean energies. The effective spectrum is dependent, particularly in quantum-counting detectors, on the signal actually acquired by the detector. This means that the effective spectrum also changes explicitly dependent upon the signal with the examination object introduced into the beam path. This change is taken into account accordingly in the combination of the spectral raw data sets to form virtual raw data sets with defined effective energies.

In a further advantageous example embodiment of the method according to the invention, the spectral raw data sets are combined to form the virtual raw data sets such that a virtual raw data set is identical to a spectral raw data set and the statistical correlation of the remaining virtual raw data sets lies below a particular limit value, and is preferably minimized. By this means, the available quantum information of the spectral raw data acquired by the detector is optimally utilized, i.e. the noise contained in the data is minimized.

Herein a combination of the methods is also possible. In such a combination of this example embodiment with the preceding embodiments, it can be considered in a certain range whether for the virtual raw data sets, mainly the noise will be minimized or particular mean or effective energies are to be obtained as well as possible. The ratio between the options can be stipulated, for example, via an input by a user.

Preferably in the method according to an embodiment of the invention for image reconstruction, water is selected as the first material. This is advantageous since in the spectral data for established computed tomography acquisition methods, water is transferred substantially linearly as a function of its irradiated length in the line integrals.

In an advantageous development of an embodiment of the invention, the material-specific maps in step d) are generated from the auxiliary image data sets using a threshold function. The image values (typically HU values) of the auxiliary image data sets serve as function arguments. The threshold function is preferably a function which assumes function values identical to zero up to a threshold value and thereabove, has a linear course. The threshold value is herein set to a value that is greater than the values which are typically assumed by the first material in the auxiliary image data sets. In this way, such regions of the auxiliary image data sets which contain mainly the first material can be ignored, i.e. set to zero. By contrast, the other regions are represented as usual.

In an advantageous embodiment of the method according to an embodiment of the invention for image reconstruction, for the second material as a material-specific map, an electron density map, an atomic number map and/or a map of attenuation coefficients are used.

The different material-specific maps are herein based on the different interaction effects of the X-ray radiation with the material. The electron density map is based substantially on the Compton effect for which the interaction in most materials is proportional to their mass density. By contrast with this, the atomic number map is based substantially on the photoelectric effect which gives information about the elemental material composition of the examination object. In particular, it is also possible for the method according to the invention to generate material-specific maps which are sensitive for materials with particular interaction properties with the X-ray radiation. An example of this is the contrast medium gadolinium which has a k-edge in the region of the typically used X-ray radiation and as a result is spectrally readily separable from other materials.

The absorption coefficient results from the total of the individual interactions (photoelectric effect, Compton scattering and possibly pair formation) and therefore permits a generalized consideration. For example, in the region of a lesion, the absorption coefficient is usually increased. The method according to the invention enables differentiation between the atomic number and the electron density, i.e. a distinction can be made, for example, on the basis of the material-specific map, between a calcification and a node.

In an advantageous iterative embodiment of the method for image reconstruction according to the invention, the steps b) to f) are repeated for a number of passes and in at least one of the steps, the synthetic projection data sets of a pass are used in the following pass as virtual raw data sets. The number of passes can, for example, herein be predefined, determined by a user or are directed according to a termination criterion such as a minimum value of contrast, signal-to-noise ratio or the like. If relevant, similarly to step a) of the method for image reconstruction according to the invention, the synthetic projection data sets can be combined anew to form virtual raw data sets before a next iterative pass.

By way of this iterative method, therefore, the synthetic projection data prepared in the previous pass are again used as input values, that is, as virtual raw data sets for a further optimization. A data set of a virtual spectral channel is thus always further monochromatized. Herein, as the number of passes increases, the respective imaging function transitions ever further into an identical image, i.e. after a certain number of passes, the data sets are so monochromatic that on further passes, they hardly become any more monochromatic.

In an advantageous development of an embodiment of the iterative method, the synthetic projection data sets of a pass are used in the following pass as virtual raw data sets in step b) and in step f), the original virtual raw data sets are used. As distinct from the first variant, herein, it is not the synthetic projection data sets of the prior pass that are used as the functional arguments of the respective imaging function, but always the original virtual raw data sets which were determined at the start of the method, i.e. in the first pass. In this variant, therefore, only the respective imaging function is iteratively improved. With an increasing number of passes, the change to the respective imaging function becomes ever smaller, so that it converges toward a limit function.

In an advantageous development of an embodiment of an iterative method for image reconstruction, the synthetic projection data sets are weighted so that they are correlated statistically as weakly as possible before they are used in the following pass as virtual raw data sets. This can take place, as already described in relation to the example embodiments of the method for image reconstruction, by way of a linear combination of the respective data sets.

Shown in FIG. 1 by way of example and coarsely schematically is a computed tomography system 1 according to an embodiment of the invention which comprises a user terminal 25 and a computed tomography device 2. The computed tomography system 1 is configured to carry out the method according to an embodiment of the invention for image reconstruction. The computed tomography device 2 comprises a patient table 12 for positioning a patient 1 as the examination object, which is displaceable along a system axis 16. The system axis 16 is also denoted below as the z-axis which is displaceable with the patient 10 into the scanning field.

It also comprises a gantry 3 with a source-detector arrangement 4, 5 which is mounted rotatable about the system axis 16. The source-detector arrangement 4, 5 has an X-ray radiation source 5 and a quantum-counting detector 4 which are oriented opposing one another so that in operation an X-ray beam emerging from the focus of the X-ray beam source 5 is incident upon the detector 4.

The detector 4 is structured for spatially-resolved acquisition of the X-ray radiation in individual pixels 17 which are arranged in a plurality of detector rows. Currently, detectors 4 are used which have a total of 64 or more rows and have a spatial resolution in the submillimeter range. For each projection, the detector 4 generates a set of projection data. The projection data herein represents the attenuation values of all the pixels 17 of an X-ray radiation attenuated by the patient 1. Depending on their energy, they are detected in separate bins of the pixels 17 of the detector 4.

The respective proportions of the projection data of all the projections which have been detected with the same energy in corresponding bins are herein one spectral raw data set SD1, SD2, . . . , SDN. The spectral raw data sets SD1, SD2, . . . , SDN are passed on to the user terminal 25 with an image reconstruction device 13 and computed by way of a method according to an embodiment of the invention to a resultant image which, for example, is displayable on a display unit 19 and/or which is stored in a memory store and/or can be sent to other systems. For this purpose, the image reconstruction device 13 comprises a combination module 14 and an optimization module 15. The user terminal 25 further comprises a keyboard 26 as the input device with which, if relevant, a user can set values for parameters in the image reconstruction.

It is known to use a computed tomography device 2 of this type for 3-D image reconstruction. In order to capture an image from an examination region (or region of interest), on rotation of the source-detector arrangement 4, 5, projection data are acquired from a plurality of different projection directions energy-resolved in bins as spectral raw data sets SD1, SD2, . . . , SDN. In the case of a spiral scan, during one rotation of the source-detector arrangement 4, 5, for example, a continuous adjustment of the patient table 12 in the direction of the system axis 16 takes place at the same time. With this type of scanning, the X-ray radiation source 5 and the detector 4 thus move on a helical path round the patient 10.

Figure 2:
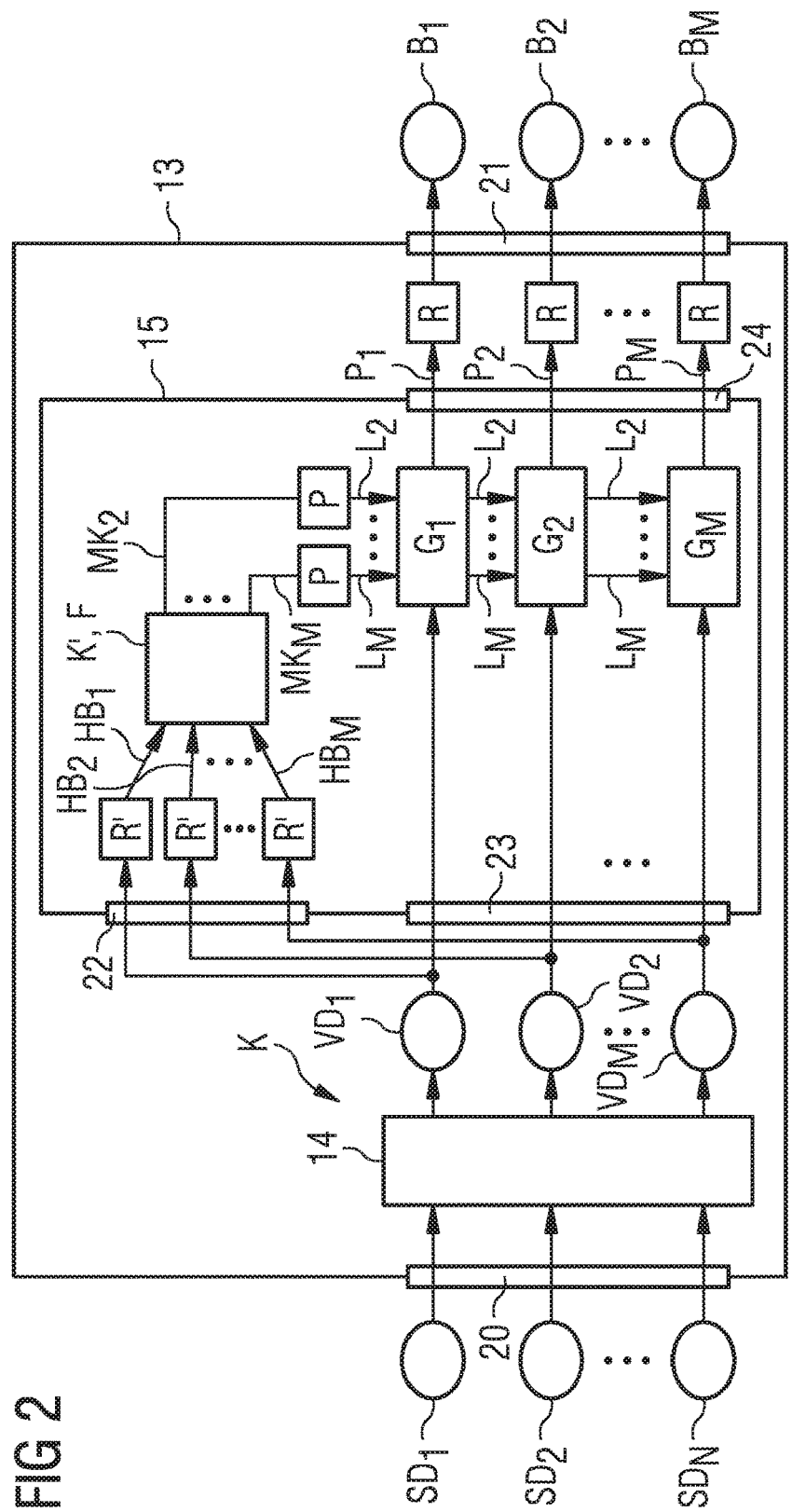
FIG. 2 is a schematic representation of an example embodiment of an image reconstruction device according to the invention with a block diagram of an example embodiment of a method according to the invention for image reconstruction.

FIG. 2 shows a schematic representation of an image reconstruction device 13 according to an embodiment of the invention with a block diagram of a method according to an embodiment of the invention for image reconstruction. The image reconstruction device 13 comprises a combination module 14 and an optimization module 15 as well as an input interface 20 and an output interface 21. The input interface 20 receives a number N of spectral raw data sets $SD_1, SD_2, \ldots, SD_N$ acquired by the computed tomography device 2 and passes them on to the combination module 14. The combination module 14 carries out a linear combination K of the spectral raw data sets $SD', SD_2, \ldots, SD_N$ and therein generates a number M of virtual raw data sets $VD_1, VD_2, \ldots, VD_M$. From the generation of the virtual raw data sets $VD_1, VD_2, \ldots, VD_M$ onward, the indices 1, 2, ..., M denote virtual spectral channels. They are thus assigned to the accordingly combined spectrum and later also to a material.

In the linear combination K, the spectral raw data sets $SD_1, SD_2, \ldots, SD_N$ are each multiplied for a virtual raw data set $VD_1, VD_2, \ldots, VD_M$ by coefficients, that is, scalar factors and subsequently added, so that depending on the selection of the operator, they have defined mean or effective energies and/or are statistically correlated as weakly as possible. The number M is preferably 3, particularly preferably 2 and is thus smaller than the number N of spectral raw data sets $SD_1, SD_2, \ldots, SD_N$, since the detector 4 usually resolves the spectrum of the X-ray radiation into more energy thresholds than currently can be usefully used for the subsequent material-dependent optimization of the reconstruction.

The optimization module 15 comprises a first input interface 22 and a second input interface 23 as well as an output interface 24. The virtual raw data sets $VD_1, VD_2, \ldots, VD_M$ are transferred from the combination module 14 both to the first input interface 22 to generate optimizing imaging functions $G_1, G_2, \ldots, G_M$ and also to the second input interface 23 as arguments for the optimizing imaging functions $G_1, G_2, \ldots, G_M$.

The virtual raw data sets $VD_1, VD_2, \ldots, VD_M$ received by the first input interface 22 are each reconstructed via a back projection R' filtered as an auxiliary measure to form auxiliary image data sets $HB_1, HB_2, \ldots, HB_M$. There follows a further optional linear combination K' of the auxiliary image data sets $HB_1, HB_2, \ldots, HB_M$ to form newly weighted auxiliary image data sets which are assigned to a material and, for example, are again statically correlated as weakly as possible. One of the auxiliary image data sets $HB_1$ is assigned to the material "water" which is selected (in accordance with step c) of the method described above). From the other M−1 auxiliary image data sets $HB_2, HB_3, \ldots, HB_M$, in each case material-specific maps $MK_2, MK_3, \ldots, MK_M$ are calculated voxel-wise via a threshold function F. These substantially illustrate the local concentrations of the respective materials, but can also represent an electron density map or an atomic number map.

Subsequently (according to step e) of the above method) by way of a virtual forward projection P with the same geometry as for the acquisition of the original data, material line integrals $L_2, \ldots, L_M$ are acquired from the material-specific maps $MK_2, MK_3, \ldots, MK_M$ for each material. Subsequently, M optimizing imaging functions $G_1, G_2, \ldots, G_M$ are generated substantially by way of a linear combination of material line integrals $L_2, \ldots, L_M$ weighted with the absorption coefficients $\mu_2, \ldots, \mu_M$. In addition thereto, the first component of the respective imaging function $G_j$ where j=1, M which is assigned to the selected material, as the function $h_j$ of the material line integrals $L_2, \ldots, L_M$, to the absorption coefficient $\mu_{ij}$ of the selected material and to the virtual raw data set $VD_1, VD_2, \ldots, VD_M$ assigned to the respective virtual spectral channel j=1, . . . , M is formed as the argument as follows:

$$G_j(VD_j;L_2,\ldots,L_M) = h_j(VD_j;L_2,\ldots,L_M)\mu_{1j} + L_2\mu_{2j} + L_3\mu_{3j} + \ldots$$

With the optimizing imaging functions $G_1, G_2, \ldots, G_M$, (in accordance with step f) of the above method), from the virtual raw data set $VD_1, VD_2, \ldots, VD_M$ as arguments, respective optimized synthetic projection data $P_1, P_2, \ldots, P_M$ is generated. This leaves the optimization module 15 via the output interface 24.

In the following step (in accordance with step g) of the above method), the synthetic projection data $P_1, P_2, \ldots, P_M$ is reconstructed in each case by way of filtered back projection R to image data sets $B_1, B_2, \ldots, B_M$. These are transferred to the output interface 21 and can then be displayed, for example, on the display unit 19 of the user terminal 25 of the computed tomography system 1 or also further transferred to arbitrary other display units and/or memory storage facilities.

Typically, all the data of the method described, that is from the spectral raw data $SD_1, SD_2, \ldots, SD_N$ to the image data $B_1, B_2, \ldots, B_M$ and, in particular, also the imaging functions $G_j$ have a dependency on parameters of the beam. Parameters of the beam are, for example, the projection angle, the channel number, the detector row and the like. This relationship exists, for example, because the X-ray spectrum changes as a function of the spacing from the rotation point due to a shaping filter. Variables such as the absorption coefficients $\mu$ naturally remain independent of the parameters of the beam.

Figure 3:
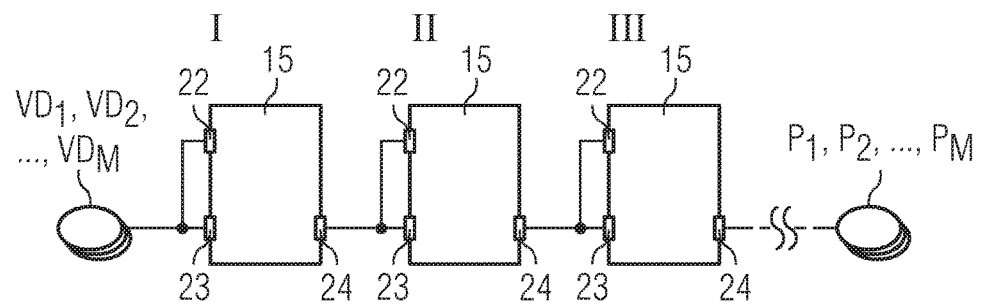
FIG. 3 is a schematic representation of an example embodiment of a first iterative method for image reconstruction according to the invention and FIG. 4 is a schematic representation of an example embodiment of a second iterative method for image reconstruction according to the invention.

FIG. 3 is an example schematic representation of a first variant of an iterative method for image reconstruction. The virtual raw data sets $VD_1, VD_2, \ldots, VD_M$ have been combined in a preparatory step via the combination module 14 from the spectral raw data sets $SD_1, SD_2, \ldots, SD_N$ (not shown here). From these, in an arbitrary number of optimization passes I, II, III, . . . optimized synthetic projection data sets $P_1, P_2, \ldots, P_M$ are generated. For this, an optimization module which is configured particularly preferably as a software module is accordingly run through multiple times. Here, as an alternative embodiment, a corresponding number of optimization modules 15 is clearly shown connected one after another. The first optimization module 15 receives the virtual raw data sets $VD_1, VD_2, \ldots, VD_M$ at both input interfaces 22, 23. Subsequently, it calculates synthetic projection data sets $P_1, P_2, \ldots, P_M$ and passes these via its output interface 24 to both input interfaces 22, 23 of the optimization module 15 arranged therebehind. This procedure is repeated for a desired number of passes. Finally, i.e. as soon as the desired degree of optimization has been achieved, the optimized synthetic projection data sets $P_1, P_2, \ldots, P_M$ are output and then reconstructed as already described to form image data sets $B_1, B_2, \ldots, B_M$ (not shown here).

Figure 4:
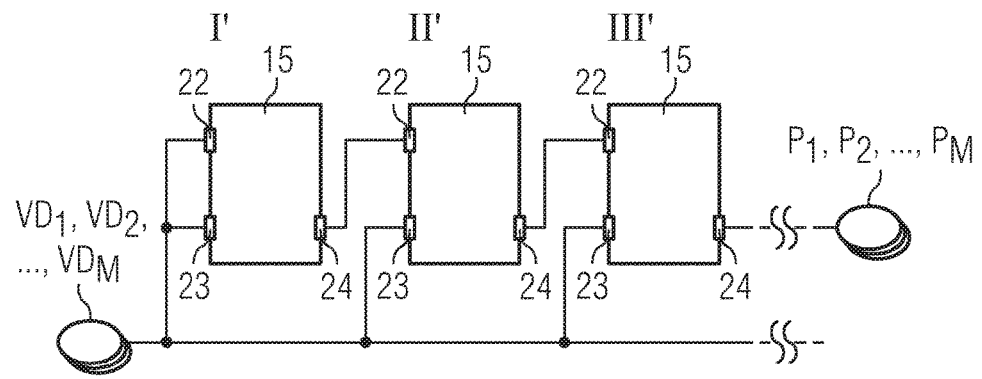

FIG. 4 shows schematically by way of example a second variant of an iterative method for image reconstruction. FIG. 4 is herein similar to FIG. 3. The difference lies in that only the first input interface 22 of the respective optimization module 15 receives the optimized synthetic projection data sets $P_1, P_2, \ldots, P_M$ from the prior optimization pass I', II', III', ... as virtual raw data sets $VD_1, VD_2, \ldots, VD_M$. By contrast, the second input interface 23 always, i.e. on each pass, receives the original virtual raw data sets $VD_1, VD_2, \ldots, VD_M$.

The method according to an embodiment of the invention enables a flexible use of the multispectral information for the reduction of radiation hardening artifacts or for calculating monochromatic images or base material images. It therefore unifies the advantages of image-based and raw data-based methods and avoids the respective disadvantages.

Finally, it should again be noted that the devices and methods described above in detail are merely example embodiments which can be modified by a person skilled in the art in a wide variety of ways without departing from the scope of the invention. Thus, synthetic absorption coefficients can also be assigned, for example, to the materials in a form such that for particular materials the absorption coefficient is set equal to zero in order to hide this material. Further, the use of the indefinite article "a" or "an" does not preclude that the relevant features can also be present plurally. Similarly, the terms "unit", "module" and "component" do not preclude the relevant components consisting of a plurality of cooperating partial components which can also be spatially distributed if necessary.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for image reconstruction based upon a first plurality of spectral raw data sets, each associated with different X-ray spectra, comprising:
   combining the spectral raw data sets to form a second plurality of virtual raw data sets;
   reconstructing a respective auxiliary image data set on the basis of each respective virtual raw data set;
   selecting a first material from a material group including a plurality of materials;
   generating material-specific maps for a number of second materials of the material group from the auxiliary image data sets;
   determining material line integrals for the second materials with forward projection of the respective material-specific map;
   determining synthetic projection data sets on the basis of the virtual raw data sets and the material line integrals for each material; and
   reconstructing at least one image data set on the basis of the synthetic projection data sets for a number of materials of the material group.

2. The method of claim 1, wherein the spectral raw data sets are combined to form the virtual raw data sets such that the virtual raw data sets have defined mean energies.

3. The method of claim 1, wherein the spectral raw data sets are combined to form the virtual raw data sets such that the virtual raw data sets have defined effective energies.

4. The method of claim 1, wherein the spectral raw data sets are combined to form the virtual raw data sets such that a virtual raw data set is identical to a spectral raw data set and the statistical correlation of the other virtual raw data sets lies below a limit value.

5. The method of claim 1, wherein water is selected as the first material.

6. The method of claim 1, wherein the material-specific maps are generated using a threshold function from the auxiliary image data sets.

7. The method of claim 1, wherein for the second materials as a material-specific map, at least one of an electron density map, an atomic number map and a map of attenuation coefficients are used.

8. The method of claim 1, wherein steps of the reconstructing of a respective auxiliary image data set, the selecting of a first material, the generating of material-specific maps, the determining of material line integrals, and the determining of synthetic projection data sets are repeated iteratively in a plurality of passes and in at least one of the steps, the synthetic projection data sets of a pass are used in the following pass as virtual raw data sets.

9. The method of claim 8, wherein the synthetic projection data sets of a pass are used in the following pass as virtual raw data sets in the reconstructing of a respective auxiliary image data set and, in the determining of synthetic projection data sets, the original virtual raw data sets are used.

10. The method as claimed in claim 8, wherein the synthetic projection data sets are weighted so that they are correlated statistically as weakly as possible before they are used in the following pass as virtual raw data sets.

11. An image reconstruction device including at least one processor, a data input interface and a data output interface wherein the at least one processor of the image reconstruction device is configured such that, for a first plurality of spectral raw data sets received via the data input interface, the at least one processor of the image reconstruction device is configured to
   combine the spectral raw data sets to form a second plurality of virtual raw data sets;
   reconstruct an auxiliary image data set on the basis of a virtual raw data set, wherein a first material is selected from a material group which comprises a plurality of materials;
   generate material-specific maps for a number of second materials of the material group from the auxiliary image data sets;

determine material line integrals for the second materials with forward projection of the respective material-specific map;

determine synthetic projection data sets on the basis of the virtual raw data sets and the material line integrals for each material; and reconstruct at least one image data set of synthetic projection data sets for a number of materials of the material group.

12. A computed tomography system, comprising:

a source-detector arrangement, including an X-ray radiation source and a detector, configured such that the detector is configured to receive radiation emitted from the X-ray radiation source in different original spectral channels as spectral raw data sets; and the image reconstruction device of claim 11.

13. A non-transitory computer program product including a computer program, directly loadable into a memory storage facility of an image reconstruction device, including program sections to carry out the method of claim 1 when the computer program is executed by at least one processor of the image reconstruction device.

14. A non-transitory computer-readable medium on which executable program sections are stored, readable in by a computer unit to carry out the method of claim 1 when the program sections are carried out by the computer unit.

15. The method of claim 1, wherein the spectral raw data sets are combined to form the virtual raw data sets such that a virtual raw data set is identical to a spectral raw data set and the statistical correlation of the other virtual raw data sets is minimized.

16. The method of claim 2, wherein the spectral raw data sets are combined to form the virtual raw data sets such that a virtual raw data set is identical to a spectral raw data set and the statistical correlation of the other virtual raw data sets lies below a limit value.

17. The method of claim 3, wherein the spectral raw data sets are combined to form the virtual raw data sets such that a virtual raw data set is identical to a spectral raw data set and the statistical correlation of the other virtual raw data sets lies below a limit value.

18. The method of claim 2, wherein the spectral raw data sets are combined to form the virtual raw data sets such that a virtual raw data set is identical to a spectral raw data set and the statistical correlation of the other virtual raw data sets is minimized.

19. The method of claim 2, wherein water is selected as the first material.

20. The method of claim 2, wherein the material-specific maps are generated using a threshold function from the auxiliary image data sets.

21. The method of claim 2, wherein for the second materials as a material-specific map, at least one of an electron density map, an atomic number map and a map of attenuation coefficients are used.

22. The method as claimed in claim 9, wherein the synthetic projection data sets are weighted so that they are correlated statistically as weakly as possible before they are used in the following pass as virtual raw data sets.

23. The method of claim 2, wherein steps of the reconstructing of a respective auxiliary image data set, the selecting of a first material, the generating of material-specific maps, the determining of material line integrals, and the determining of synthetic projection data sets are repeated iteratively in a plurality of passes and in at least one of the steps, the synthetic projection data sets of a pass are used in the following pass as virtual raw data sets.

24. The method of claim 23, wherein the synthetic projection data sets of a pass are used in the following pass as virtual raw data sets in the reconstructing of a respective auxiliary image data set and, in the determining of synthetic projection data sets, the original virtual raw data sets are used.

25. The method as claimed in claim 23, wherein the synthetic projection data sets are weighted so that they are correlated statistically as weakly as possible before they are used in the following pass as virtual raw data sets.

* * * * *